United States Patent [19]

Rudnic et al.

[11] Patent Number: 5,326,570
[45] Date of Patent: Jul. 5, 1994

[54] ADVANCED DRUG DELIVERY SYSTEM AND METHOD OF TREATING PSYCHIATRIC, NEUROLOGICAL AND OTHER DISORDERS WITH CARBAMAZEPINE

[75] Inventors: Edward M. Rudnic, Gaithersburg; George W. Belendiuk, Potomac, both of Md.

[73] Assignee: Pharmavene, Inc., Gaithersburg, Md.

[21] Appl. No.: 734,541

[22] Filed: Jul. 23, 1991

[51] Int. Cl.⁵ ................................. A61K 9/54
[52] U.S. Cl. ........................ 424/458; 424/451; 424/452; 424/457; 424/459; 424/465; 424/468; 424/469; 424/489; 424/490
[58] Field of Search ............ 424/451, 465, 457, 489, 424/459, 458, 468, 469, 490, 452; 544/152

[56] References Cited

U.S. PATENT DOCUMENTS

| | | | |
|---|---|---|---|
| 4,606,909 | 8/1986 | Bechgaard et al. | 424/481 |
| 4,794,001 | 12/1988 | Mehta et al. | 424/457 |
| 4,801,460 | 1/1989 | Goertz et al. | 424/465 |
| 4,857,336 | 8/1989 | Khanna et al. | 424/486 |
| 4,942,182 | 7/1990 | Weiss et al. | 424/10 |
| 4,980,170 | 12/1990 | Schneider et al. | 424/451 |
| 5,009,894 | 4/1991 | Hsiao | 424/451 |
| 5,023,272 | 6/1991 | Burch et al. | 544/152 |

Primary Examiner—Thurman K. Page
Assistant Examiner—James M. Spear
Attorney, Agent, or Firm—Elliot M. Olstein; Susan A. Capello

[57] ABSTRACT

The present invention relates to a composition and method of treating a patient by administering carbamazepine in a pharmaceutical dosage form capable of maintaining the patient's blood concentration at from about 4 μg/ml to about 12 μg/ml over at least a 12 hour period, where the blood concentration of carbamazepine does not vary by more than 60 percent.

25 Claims, 1 Drawing Sheet

DOSAGE FORM COMPONENTS AND TARGET DISSOLUTION

DOSAGE FORM COMPONENTS AND TARGET DISSOLUTION

ADVANCED DRUG DELIVERY SYSTEM AND METHOD OF TREATING PSYCHIATRIC, NEUROLOGICAL AND OTHER DISORDERS WITH CARBAMAZEPINE

The present invention relates to a method of delivery for carbamazepine which will provide steady and consistent blood levels of carbamazepine. The blood levels of carbamazepine are within a therapeutic range required for the treatment of epilepsy as well as other psychiatric, neurological and other disorders.

Carbamazepine is an iminostilbene derivative that is used clinically to treat seizure disorders, trigeninal neuralgia, and most recently, manic depressive illness.

The present invention provides a method and composition for delivery of carbamazepine which provides steady and consistent blood levels of carbamazepine within a therapeutic range. The therapeutic range is from about 6 $\mu$g/ml to about 12 $\mu$g/ml of carbamazepine over a period of time. Blood levels of carbamazepine of less than 4 $\mu$g/ml have been found to be ineffective in treating clinical disorders and blood levels greater than 12 $\mu$g/ml have been found to be likely to result in undesirable side effects such as neuromuscular disturbances, cardiovascular and gastrointestinal effects.

The present invention provides for the maintenance of blood levels of carbamazepine (C) so as to minimize Cmax/Cmin variation or fluctuation. An acceptable fluctuation in the blood level Cmin/Cmax ratio would be a range of from about 0.6 to about 1.0. Most preferably, the variation or fluctuation would range from about 0.8 to about 1.0.

The present invention maintains a therapeutic range of blood levels of carbamazepine effective for the treatment of disorders which include but are not limited to depression, trigeminal; neuralgia; chronic pain states; headaches; addictive states for: cocaine, alcohol, opiates and nicotine; other obsessive compulsive disorders and cardiovascular disease.

An embodiment of the present invention provides for a sustained release method of delivery of carbamazepine which is to be administered at least once a day, preferably twice a day; therefore, in accordance with an aspect of the present invention there is provided a steady and consistent blood level of carbamazepine within therapeutic range of from about 4 $\mu$g/ml to about 12 $\mu$g/ml, over a time period of at least 12 hours. In accordance with the present invention, within the hereinabove noted therapeutic range, the blood concentration of carbamazepine varies by not more than 60 percent and preferably by not more than 40 percent and most preferably by not more than 20% over a period of at least twelve hours.

The method of delivery of carbamazepine of the present invention provides for the following routes of administration sublingual, transmucosal, transdermal, parenteral and preferably oral. Parenteral administration would require an amount of carbamazepine of from about 100 mg to about 1000 mg per 12 hours. The dosage forms may include but are not limited to liquids, tablets, capsules, sprinkle dosage forms, chewable tablets and transdermal patches.

The sustained-release method of delivery of the present invention may be accomplished by administering multiple single unit dosage forms of equal or varying concentration of carbamazepine. Each such unit would be designated to release its contents at varying times over at least a twelve hour time period so as to maintain a carbamazepine blood level within the therapeutic range previously described.

A preferred embodiment of the present invention provides for that the patient to be treated, ingest at a single point in time a dosage form containing carbamazepine capable of maintaining the patient's blood concentration at from about 4 $\mu$g/ml to about 12 $\mu$g/ml over at least a 12 hour time period, where the blood concentration of carbamazepine does not vary by more than 20%.

Such a dosage form may consist of one or more units, having the same or varying concentrations of carbamazepine, designed to release its contents at varying times so as to maintain a carbamazepine blood concentration level within the therapeutic range and for the time period previously described.

One preferred embodiment may comprise one single dosage form which contains multiple units within it, which are capable of releasing their contents at varying times. A second embodiment of the single dosage form, may also be to consist of one unit capable of immediately releasing a concentration of carbamazepine, then sustained-releasing carbamazepine at other time points as necessary to maintain blood levels within the therapeutic range. A third embodiment may be for the dosage form to be in multiple separate units capable of releasing carbamazepine at varying times, the separate multiple units as described above would all be ingested by the patient to be treated at the same time point.

Another embodiment of the present invention provides for a composition for treating a patient comprising an effective amount of carbamazepine and a pharmaceutically acceptable carrier which are sufficient for maintaining a blood concentration of carbamazepine within the therapeutic range and as described above.

Using either dosage form it is preferred that the dose of carbamazepine administered each 24 hour period is from about 800 mg to about 1200 mm. The dose is adjusted by the administering physician based upon the age, sex and weight of the patient to maintain therapeutic blood levels of carbamazepine.

Since carbamazepine is needed to be absorbed into the bloodstream over at least a twelve-hour period, it is preferred that the drug be administered in a dosage form that will reliably remain in the GI tract, in a sufficiently high region as to favor absorption.

To achieve and maintain the therapeutic range, a dose of from about 400 to about 600 mg per 12 hour period of carbamazepine makes it necessary to have a reasonably high loading of drug in the pellets. Because of this, it is preferred to have greater than 30% (W/W) of the pellet content as carbamazepine. It is preferable to have as great a concentration as possible, and therefore ideally as much as 95% (W/W) of each pellet would consist of the drug. It may not be practical to obtain this high loading of carbamazepine for all combinations of ingredients identified this application.

The term W/W as used herein is representative of a weight to weight ratio of the material specified to the weight of the unit dosage form as a whole.

For carbamazepine, it is preferred to have three different types of units in a single form multiple-unit dosage form. The first unit is an immediate release dosage form, preferably in pellet form. This component can also be a powder if necessary. In either case, the pellet should have a surface-active agent such as sodium lauryl sulfate, sodium monoglycerate, sorbitan monooleate, polyoxyethylene sorbitan monooleate, glyceryl monostearate, glyceryl monooleate, glyceryl monobutyrate, any one of the Pluronic line of surface-active polymers, or any other suitable material with surface active properties or any combination of the above. Preferably the surface-active agent would be a combination of sodium monoglycerate and sodium lauryl sulfate. The concentration of these materials in this component can range from about 0.05 to about 10.0% (W/W).

The pellet should be made via a suitable process which makes the dosage form into a reasonably round unit. This process can be, for example, simple granulation, followed by seiving; extrusion and marumerization; rotogranulation; or any agglomeration process which results in a pellet of reasonable size and robustness. As stated earlier, it is also possible to have this immediate release component as a powder, although the preferred form is a pellet due to mixing and de-mixing considerations.

The materials to be admixed along with the drug and surfactant for this first pellet should possess sufficient binding properties to allow agglomeration to occur. These materials can be, but are not limited to, microcrystalline cellulose (such as Avicel), corn starch, pregelatinized starch (such as Starch 1500 or National 1551), potato starch, sodium carboxymethylated starch, sodium carboxymethylated cellulose, hydroxypropylmethyl cellulose, hydroxypropylcellulose, hydroxyethylcellulose, ethylcellulose, as well as any cellulose ether. In addition, any binder material such as gums (ex. Guar Gum) natural binders and derivatives such as alginates, chitosan, gelatin and gelatin derivatives, are also useful. Synthetic polymers such as polyvinylpyrrolidone (PVP), acrylic acid derivatives (Eudragit, Carbopol, etc.) and polyethylene glycol (PEG) are also useful as binders and matrix formers for the purpose of this invention. It may be useful to have these materials present in the range of from about 1.0 to about 60.0% (W/W) either in total, or individually in combination with one another. Preferably, these materials should be present in the range of from about 30 to about 50 percent (W/W).

It may also be necessary to incorporate a disintegrant into these pellets in order to facilitate dissolution of the active ingredient. For this purpose, any suitable tablet disintegrant can be utilized here, such as cross-linked sodium carboxymethylcellulose (Ac-Di-Sol), cross-linked sodium carboxymethyl starch (Explotab, Primojel), cross-linked PVP (Plasdone XL) or any other material possessing tablet disintegrant properties.

The second pellet should have a sustained release profile, and needs to be able to address the changing pH of the GI tract, and its effect on the absorption of carbamazepine. This pellet should have all of the ingredients as mentioned for pellet A, as well as some organic acid which will be useful to reduce the pH of the microenvironment of the pellet, and thus facilitate dissolution. These materials are, but not limitd to, citric acid, lactic acid, tartaric acid, or other suitable organic acids. These materials should be present in concentrations of from about 0 to about 15.0% (W/W), preferably these materials would be present in concentrations of from about 5.0 to about 10.0 percent (W/W). The process for manufacturing these pellets is consistent to the process described above for the previous pellet.

In addition to the pellet, this component should have a controlling coat applied to the surface of the pellet such that the release of the drug from the pellet is controlled and released over a 6–10 hour period. The materials used for this purpose can be, but are not limited to, ethylcellulose, hydroxypropylmethylcellulose, hydroxypropylcellulose, hydroxyethylcellulose, methylcellulose, nitrocellulose, carboxymethylcellulose, and any other cellulose ether, as well as copolymers of ethacrylic acid and methacrylic acid (Eudragit), or any other acrylic acid derivative (Carbopol, etc.) can be used. In addition, an enteric coating material can also be employed, either singularly, or in combination to the above non-pH sensitive coatings. These materials include, but are not limited to, hydroxypropylmethylcellulose phthalate and the phthalate esters of all the cellulose ethers. In addition, phthalate esters of the acrylic acid derivatives (Eudragit), or cellulose acetate phthalate. These coating materials can be employed in coating the surfaces in a range of from about 1.0% (W/W) to about 25% (W/W). Preferably these coating materials should be in a range of from about 8.0 to about 12.0 percent (W/W).

The third component in this system should be qualitatively similar to pellet B, in that the manufacturing process for producing this pellet is consistent with that of the first two pellets, and the microenvironment inside the pellet should be consistent with that of pellet B. However, this pellet should have some internal component for breaking down in the pH of the lower GI tract. Thus, it will be necessary to include some enteric or pH sensitive material into the pellet to facilitate erosion and breakdown in the lower GI tract. This material can be, but is not limited to, cellulose acetate phthalate, hydroxypropylmethylcellulose phthalate, any additional cellulose ether phthalates, any of the acrylic acid derivative phthalates (Eudragit), as well as any enteric coating material, such as shellac, zein, or others. The concentration of these materials in the pellet should be from about 1.0 to about 15.0% (W/W), preferably the concentration of amterials should be from about 5.0 to about 10.0 percent (W/W).

The coating of this third pellet should be similar to the coating for pellet B, except that it should have a considerable pH sensitivity associated with it. Therefore, it would be desirable to coat pellet C with any of the pH sensitive, or enteric coating materials listed above, either singularly, or in combination with any coating material mentioned above. The coating level of this pellet should range from about 1.0 to about 15.0% (W/W), preferably the concentration of materials should be from about 5.0 to about 12.0 percent (W/W).

BRIEF DESCRIPTION OF THE DRAWINGS

Each pellet should have its own dissolution profile associated with the formulation assigned to it. The target dissolution curves for the three pellets can be seen in FIG. 1.

This FIGURE shows a schematic of the three pellets, as well as the target dissolution for the materials. Depending on the formulation chosen in this invention, the exact ratios of each of the pellets may need to be adjusted. The amount of pellet A in the formulation should preferably range from about 5.0 to about 25.0%. The amount of Pellet B in the dosage form should range from about 15.0 to about 70.0%. The dosage form for Pellet C should be in a range of from about 10.0 to about 50.0%.

Figure 1:
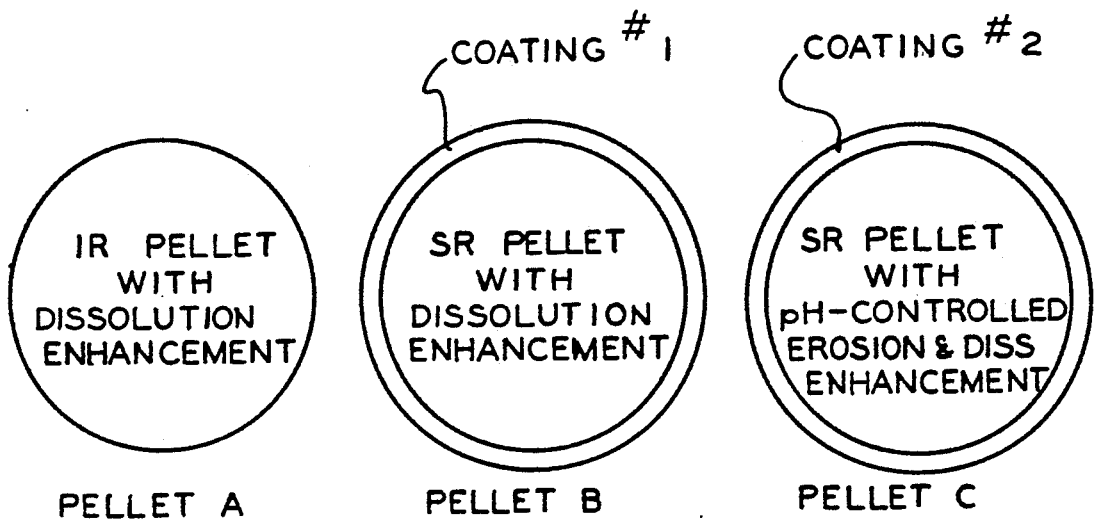
Figure 1:
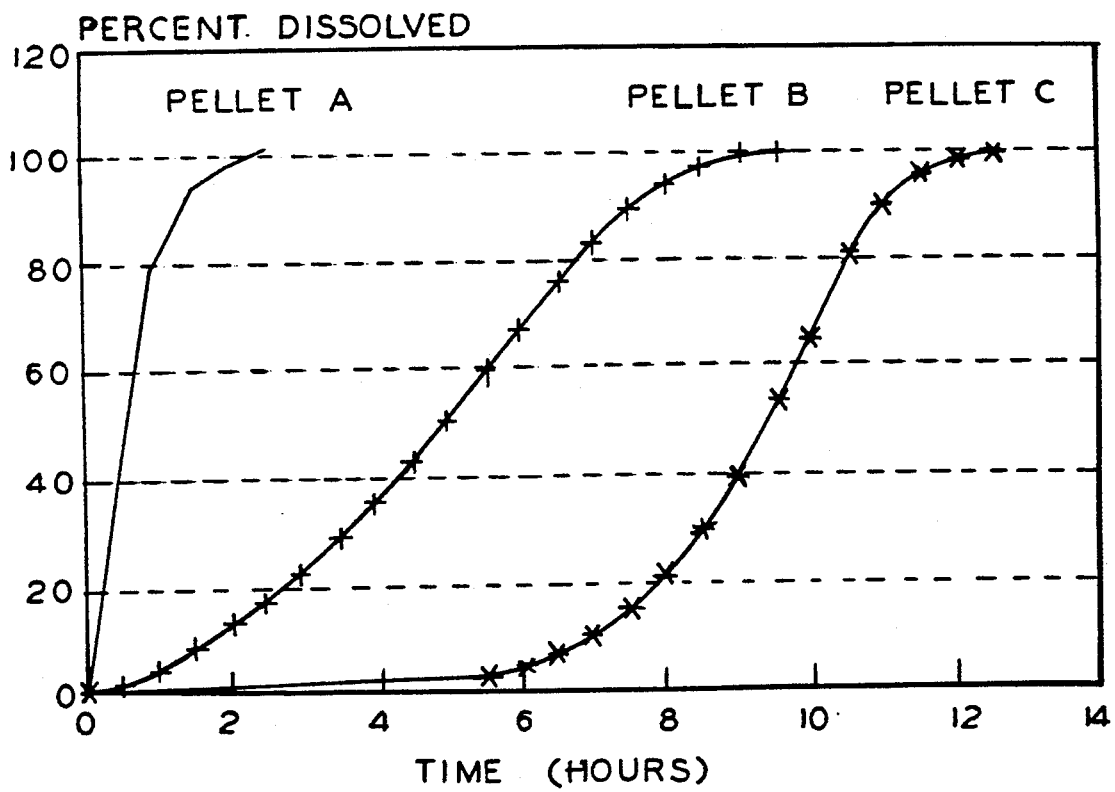

While the present invention has been described in conjunction with specific embodiments thereof, it is evident that many alternatives, modifications and variations will be apparent to those skilled in the art in view of the foregoing description. Accordingly, the plenary invention in intended to embrace all such alternatives, modifications and variations as falling within the broadest scope and spirit of the described invention.

The following examples illustrate the invention in more detail without limiting the scope thereof.

EXAMPLES

The examples are presented in three groups, one for each pellet type as described above.

| Pellet A: Immediate Release Component | Percent | Kilograms |
|---|---|---|
| Example 1: | | |
| Microcrystalline Cellulose, N.F. (MCC) (Avicel PH-101/102, Emcocel, etc.) | 40.0 | 0.4 |
| Hydroxypropylmethylcellulose (HPMC) (Methocel E5/E50/K5/K50) | 2.5 | 0.025 |
| Croscarmellose, Type A, N.F. (Ac-Di-Sol) | 2.0 | 0.02 |
| Sodium Lauryl Sulfate (SLS) | 0.1 | 0.001 |
| Carbamazepine | 55.4 | 0.554 |
| Total | 100.0 | 1.000 |
| Example 2: | | |
| MCC | 40.0 | 0.4 |
| HPMC | 5.0 | 0.05 |
| Sodium Starch Glycolate, N.F. (Explotab, Primojel) | 8.0 | 0.08 |
| SLS | 0.3 | 0.003 |
| Carbamazepine | 46.7 | 0.467 |
| Total | 100.0 | 1.000 |
| Example 3: | | |
| MCC | 20.0 | 0.2 |
| Pre-gelatinized Starch (STARCH 1500, National 1551) | 15.0 | 0.15 |
| Croscarmellose | 5.0 | 0.05 |
| Corn Starch, U.S.P. (as paste) | 5.0 | 0.05 |
| Dioctyl Sodium Sulfosuccinate (DDS) | 0.5 | 0.005 |
| Carbamazepine | 54.5 | 0.545 |
| Total | 100.0 | 1.000 |
| Example 4: | | |
| MCC | 15.0 | 0.15 |
| MCC/Carboxymethyl Cellulose (CMC) (Avicel RC Grade) | 15.0 | 0.15 |
| Croscarmellose | 5.0 | 0.05 |
| SLS | 0.5 | 0.005 |
| Carbamazepine | 64.5 | 0.645 |
| Total | 100.0 | 1.000 |
| Example 5: | | |
| MCC/CMC | 20.0 | 0.2 |
| Croscarmellose | 3.0 | 0.03 |
| Sodium Starch Glycolate | 5.0 | 0.05 |
| HPMC | 8.0 | 0.08 |
| DDS | 0.5 | 0.005 |
| Carbamazepine | 63.5 | 0.635 |
| Total | 100.0 | 1.000 |
| Example 6: | | |
| MCC | 10.0 | 0.10 |
| MCC/CMC | 10.0 | 0.10 |
| Croscarmellose | 5.0 | 0.05 |
| DDS | 0.5 | 0.005 |
| Carbamazepine | 74.5 | 0.745 |
| Total | 100.0 | 1.000 |
| Example 7: | | |
| MCC/CMC | 25.0 | 0.25 |
| Polyacrylic Acid (Carbomer) | 10.0 | 0.1 |
| SLS | 0.2 | 0.002 |
| Sodium Starch Glycolate | 7.5 | 0.075 |
| Carbamazepine | 57.3 | 0.573 |
| Total | 100.0 | 1.000 |
| Example 8: | | |
| MCC | 30.0 | 0.30 |
| HPMC | 7.5 | 0.075 |
| Croscarmellose | 5.0 | 0.05 |
| Sodium bis-(2-ethylhexyl)sulfo-succinate (Aerosol OT) | 1.5 | 0.015 |
| Carbamazepine | 56.0 | 0.560 |
| Total | 100.0 | 1.000 |
| Example 9: | | |
| MCC | 25.0 | 0.25 |
| HPMC | 5.0 | 0.05 |
| Mono/Di/Tri-glyceride Mixture (Atmul-84S) | 10.0 | 0.1 |
| SLS | 0.5 | 0.005 |
| Carbamazepine | 59.5 | 0.595 |
| Total | 100.0 | 1.000 |
| Example 10: | | |
| MCC | 25.0 | 0.25 |
| Polyvinylpyrrolidone (PVP) (Plasdone) | 8.0 | 0.08 |
| Sodium Monoglycerate (Myvaplex) | 8.0 | 0.08 |
| SLS | 0.35 | 0.0035 |
| Carbamazepine | 58.65 | 0.5865 |
| Total | 100.0 | 1.0000 |
| Example 11: | | |
| MCC | 30.0 | 0.3 |
| HPMC | 5.0 | 0.05 |
| Sodium Monoglycerate | 8.0 | 0.08 |
| Tartaric Acid | 5.0 | 0.05 |
| SLS | 0.2 | 0.002 |
| Carbamazepine | 51.8 | 0.518 |
| Total | 100.0 | 1.000 |
| Coating: | | |
| Ethacrylic/Methacrylic Acid Esters (Eudragit RS100) | 45.0 | 0.45 |
| Ethacrylic/Methacrylic Acid Esters (Eudragit RL100) | 45.0 | 0.45 |
| Propylene Glycol | 9.0 | 0.09 |
| Talc | 1.0 | 0.01 |
| Total | 100.0 | 1.00 |
| Example 12: | | |
| Same core pellet as in example 11 | | |
| Coating: | | |
| HPMC (Methocel E50) | 45.0 | 0.45 |
| Ethylcellulose (Ethocel) | 45.0 | 0.45 |
| Polyethylene Glycol 400 (PEG400) | 10.0 | 0.10 |
| Total | 100.0 | 1.00 |
| Example 13: | | |
| Same core pellet as in example 11 | | |
| Coating: | | |
| HPMC | 20.0 | 0.20 |
| Ethylcellulose | 70.0 | 0.70 |
| PEG400 | 10.0 | 0.10 |
| Total | 100.0 | 1.00 |
| Example 14: | | |
| MCC | 15.0 | 0.15 |
| MCC/CMC Mixture | 15.0 | 0.15 |
| Citric Acid | 6.0 | 0.06 |
| DSS | 0.8 | 0.008 |
| Carbamazepine | 63.2 | 0.632 |
| Total | 100.0 | 1.000 |
| Coating: | | |
| HPMC (Methocel K5M) | 10.0 | 0.10 |
| HPMC (Methocel E50) | 14.0 | 0.14 |
| Ethylcellulose | 66.0 | 0.66 |
| PEG400 | 10.0 | 0.10 |
| Total | 100.0 | 1.00 |
| Example 15: | | |
| Core pellet from example 14 | | |
| Coating from example 11 | | |
| Example 16: | | |
| Core pellet from example 14 | | |
| Coating from example 12 | | |
| Example 16: | | |
| Core pellet from example 14 | | |
| Coating from example 13 | | |
| Example 17: | | |
| MCC | 30.0 | 0.3 |
| PVP | 8.0 | 0.08 |
| Mono/Di/Tri-Glyceride Mixture | 8.0 | 0.08 |

-continued

| | Percent | Kilogram |
|---|---|---|
| SLS | 0.3 | 0.003 |
| Tartaric Acid | 7.5 | 0.075 |
| Carbamazepine | 46.2 | 0.462 |
| Total | 100.0 | 1.000 |

Coating:
Coating from example 11

Example 18:
Core pellet from example 17
Coating from example 12

Example 19:
Core pellet from example 17
Coating from example 13
Core pellet from example 17
Coating from example 14

Pellet C: Delayed Release Component

Example 21:
Core Pellet:

| | Percent | Kilogram |
|---|---|---|
| MCC | 25.0 | 0.25 |
| Hydroxypropylmethylcellulose Phthalate (HPMCP) | 10.0 | 0.10 |
| Tartaric Acid | 10.0 | 0.10 |
| Sodium Monoglycerate | 7.5 | 0.075 |
| DSS | 0.5 | 0.005 |
| Carbamazepine | 47.0 | 0.470 |
| Total | 100.0 | 1.000 |

Coating:

| | Percent | Kilogram |
|---|---|---|
| Cellulose Acetate Phthalate (CAP) | 60.0 | 0.60 |
| Ethylcellulose | 25.0 | 0.25 |
| PEG400 | 15.0 | 0.15 |
| Total | 100.0 | 1.00 |

Example 22:
Core pellet from example 21
Coating:

| | Percent | Kilogram |
|---|---|---|
| Ethacrylic/Methacrylic Acid Esters (Eudragit line of enteric polymers) | 85.0 | 0.85 |
| Propylene Glycol | 14.0 | 0.14 |
| Talc | 1.0 | 0.01 |
| Total | 100.0 | 1.00 |

Example 23:
Core pellet from example 21
Coating:

| | Percent | Kilogram |
|---|---|---|
| CAP | 65.0 | 0.65 |
| HPMCP | 15.0 | 0.15 |
| PEG 400 | 10.0 | 0.10 |
| PEG 8000 | 10.0 | 0.10 |
| Total | 100.0 | 1.00 |

Core Pellet:

| | Percent | Kilogram |
|---|---|---|
| MCC | 25.0 | 0.25 |
| Mono/Di/Tri-glyceride Mixture | 15.0 | 0.15 |
| Tartaric Acid | 10.0 | 0.10 |
| CAP | 10.0 | 0.10 |
| DSS | 0.8 | 0.8 |
| Carbamazepine | 39.2 | 0.392 |
| Total | 100.0 | 1.000 |

Coating as in example 21

Example 25:
Core pellet as in example 24
Coating as in example 22

Example 26:
Core Pellet as in example 24
Coating as in example 23

Example 27:
Core pellet as in example 24
Coating:

| | Percent | Kilogram |
|---|---|---|
| Shellac | 85.0 | 0.85 |
| Mineral Oil | 13.0 | 0.13 |
| SLS | 0.5 | 0.005 |
| Talc | 1.5 | 0.015 |
| Total | 100.0 | 1.000 |

Example 28:
Core pellet as in example 21
Coating as in example 27

What is claimed is:

1. A drug delivery system for the oral administration of carbamazepine, comprising:
   (a) a sustained release unit containing carbamazepine;
   (b) an immediate release unit containing carbamazepine; and
   (c) an enteric release unit containing carbamazepine, said combination of components (a), (b), and (c) containing a therapeutically effective amount of carbamazepine.

2. A method for treating a patient with carbamazepine, comprising: orally administering to the patient the system of claim 1.

3. The system of claim 1 wherein said components (a), (b) and (c) are present in a tablet.

4. The system of claim 1 wherein said components (a), (b) and (c) are present in a capsule.

5. The system of claim 1 wherein said components (a), (b) and (c) are present in a single dosage form.

6. The system of claim 1 wherein said components (a), (b), and (c) are in a pellet form and are present in a single dosage form.

7. The system of claim 6 wherein the single dosage form is a capsule.

8. The system of claim 1 wherein said system provides a therapeutically effective amount over a 12 hour period.

9. The system of claim 1 wherein said system comprising components (a), (b) and (c) contains carbamazepine in an amount from about 400 mg to about 600 mg.

10. The system of claim 1 wherein the system provides blood dosage levels of carbamazepine which do not vary by more than 60% over a 12 hour period.

11. The system of claim 10 wherein the blood dosage levels do not vary by more than 20% over a 12 period.

12. A system as in claim 1, wherein each of the units includes a surfactant.

13. A system as in claim 12, wherein the sustained release unit and the enteric release unit each contain an organic acid to maintain an acidic environment in the units.

14. A system as in claim 12, wherein said surfactant is sodium lauryl sulfate.

15. A system as in claim 1, wherein said sustained release unit is present in an amount ranging from about 5.0% to about 25.0% (w/w), said immediate release unit is present in an amount ranging from about 15.0% to about 70.0% (w/w) and said enteric release unit is present in an amount ranging from about 10.0% to about 50.0% (w/w).

16. A system as in claim 15, wherein said sustained release unit is coated with a coating material in an amount ranging from about 1.0% to about 25% (w/w) and said enteric release unit is coated with a coating material in an amount ranging from about 1.0% to about 15.0% (w/w).

17. A system as in claim 1, wherein the carbamazepine in said sustained release unit is released from said unit over a period from about 6 to about 10 hours.

18. A method of treating a patient with carbamazepine comprising: orally administering to said patient a composition which contains,
   (a) an immediate release unit containing carbamazepine;
   (b) a sustained release unit containing carbamazepine;
   (c) an enteric release unit containing carbamazepine; said components (a), (b), and (c) containing a therapeutically effective amount of carbamazepine.

19. A method as in claim 18, wherein said components (a), (b), (c) being administered in a combined amount to maintain a blood dosage level of carbamazepine within a range of from about 4 μg/ml to about 12 μg/ml for a period of at least 12 hours.

20. A method as in claim 18, wherein the components being administered contain a combined amount of carbamazepine of from about 400 mg to about 600 mg.

21. A method as in claim 19, wherein the blood dosage level of carbamazepine does not vary by more that 60 percent per 12 hour period.

22. A method as in claim 20, wherein the blood dosage level of carbamazepine within said range does not vary by more than 20 percent per 12 hour period.

23. A method as in claim 18, wherein each of the units includes a surfactant.

24. A method as in claim 22, wherein said surfactant is sodium lauryl sulfate.

25. A method as in claim 23, wherein said sustained release unit and said enteric release unit each contain an organic acid to maintain an acidic environment in the units.

* * * * *